United States Patent [19]

Bentley et al.

[11] 4,332,724
[45] Jun. 1, 1982

[54] PROCESS FOR PREPARING 4,5,6,7-TETRAHYDRO-7-OXOBENZO[B]THIOPHENES AND 1,2,3,4-TETRAHYDRO-4-OXONAPHTHALENES

[75] Inventors: Terence J. Bentley, Cranbury; William H. Gastrock, Hightstown; Goro Asato, Titusville, all of N.J.

[73] Assignee: American Cyanamid Co., Stamford, Conn.

[21] Appl. No.: 851,992

[22] Filed: Nov. 16, 1977

Related U.S. Application Data

[63] Continuation of Ser. No. 713,768, Aug. 12, 1976, abandoned.

[51] Int. Cl.³ .................. C07D 209/34; C07D 207/24; C07D 333/24; C07C 125/06
[52] U.S. Cl. .................. 260/326 S; 549/51; 560/28; 564/45; 564/44; 564/48; 564/161; 564/166; 564/176; 564/215; 548/465; 548/473; 548/527; 548/545; 548/548
[58] Field of Search .................. 260/332.2 R, 332.3 P, 260/586 P, 590 C, 326 S, 326.5 SA, 326.5 C, 326 A, 326 R; 549/51; 560/28; 564/45, 44, 48, 161, 166, 176, 215

[56] References Cited

U.S. PATENT DOCUMENTS 3,546,303 12/1970 Hornberger .................. 260/586
3,994,924 11/1976 Asato .

OTHER PUBLICATIONS

House "Modern Synthesis Reactions", 2nd ed. (1972), p. 278.

Primary Examiner—Alan Siegel
Attorney, Agent, or Firm—H. G. Jackson

[57] ABSTRACT

There is provided a process for the preparation of an amido or an ureido derivative of certain 4,5,6,7-tetrahydro-7-oxobenzo[b]thiophenes or certain 1,2,3,4-tetrahydro-4-oxonaphthalenes which can be employed as an animal growth regulant. The process comprises: oxidizing in the presence of a cobalt catalyst a compound having the formula:

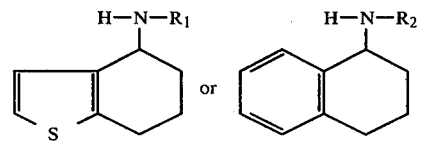

wherein $R_1$ and $R_2$ are each a substituent selected from the group consisting of alkanoyl $C_1$–$C_7$, halogen-substituted alkanoyl $C_1$–$C_7$, carboalkoxy $C_1$–$C_4$,

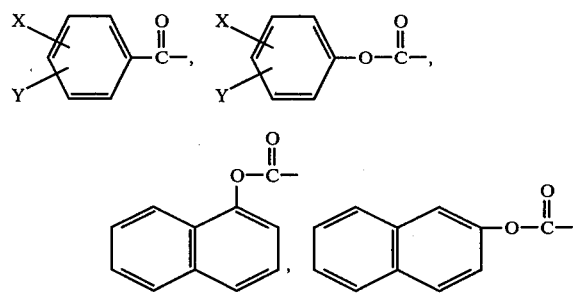

and

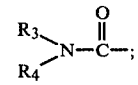

$R_3$ is selected from the group consisting of hydrogen and alkyl $C_1$–$C_4$; $R_4$ is selected from the group consisting of hydrogen, alkyl $C_1$–$C_8$, alkanoyl $C_2$–$C_4$, halogen-substituted alkanoyl ($C_2$–$C_4$), and

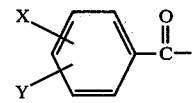

and when the

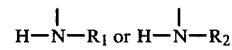

moiety is cyclized each represents a moiety selected from the group consisting of succinimido, maleimido and phthalimido; X and Y are each a radical selected from the group consisting of hydrogen, fluorine, chlorine, bromine, iodine, nitro, alkyl $C_1$–$C_4$; the racemic mixtures and the optical isomers thereof.

25 Claims, No Drawings

PROCESS FOR PREPARING 4,5,6,7-TETRAHYDRO-7-OXOBENZO[B]THIOPHENES AND 1,2,3,4-TETRAHYDRO-4-OXONAPHTHALENES

This is a continuation, of application Ser. No. 713,768 filed Aug. 12, 1976, now abandoned.

The present invention relates to a novel process for the preparation of amido and ureido derivatives of 4,5,6,7-tetrahydro-7-oxobenzo[b]thiophene and 1,2,3,4-tetrahydro-4-oxo-naphthalene which are useful as animal growth regulants. More particularly, it relates to the oxidation of amido or ureido derivatives of 4,5,6,7-tetrahydro-benzo[b]thiophenes or 1,2,3,4-tetrahydro-4-oxo-naphthalenes. Still more particularly, it is concerned with a process for the preparation of an amido or an ureido derivative of certain 4,5,6,7-tetrahydro-7-oxobenzo[b]thiophenes or certain 1,2,3,4-tetrahydro-4-oxonaphthalenes which comprises oxidizing in the presence of a cobalt catalyst a compound having the formula:

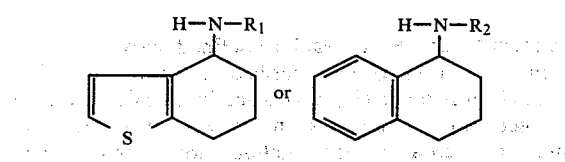

wherein $R_1$ and $R_2$ are each a substituent selected from the group consisting of alkanoyl $C_1-C_7$, halogen-substituted alkanoyl $C_1-C_7$, carboalkoxy $C_1-C_4$,

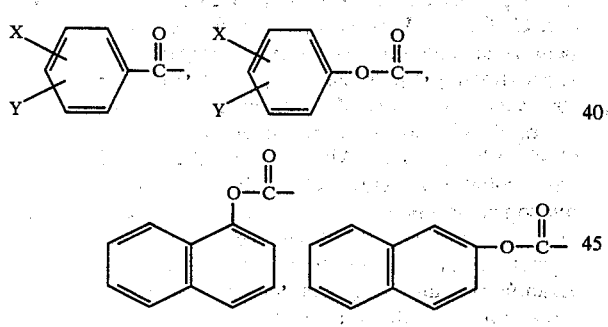

$R_3$ is a radical selected from the group consisting of hydrogen and alkyl $C_1-C_4$; $R_4$ is a radical selected from the group consisting of hydrogen, alkyl $C_1-C_8$, and alkanoyl ($C_2-C_4$) halogen-substituted alkanoyl ($C_2-C_4$) and

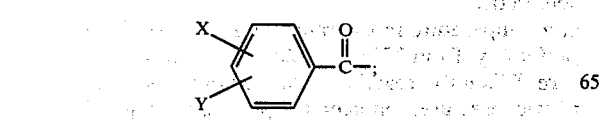

and when the

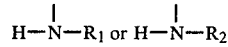

moiety is cyclized, each represents a moiety selected from the group consisting of succinimido, maleimido and phthalimido; X and Y are each a radical selected from the group consisting of hydrogen, fluorine, chlorine, bromine, iodine, nitro, alkyl $C_1-C_4$; the racemic mixtures and the optical isomers thereof.

The above-identified tetrahydro-oxobenzo[b]-thienylureas are useful as animal growth promoting agents as disclosed in German Offenlegungschrift No. 2,501,788, published on July 7, 1975, and in an application for U.S. Pat., Ser. No. 532,449, filed Dec. 13, 1974. Further, the above-identified tetrahydro-oxonaphthylureas and their use as animal growth promoting agents are disclosed in an application of G. Asato, for U.S. Pat., Ser. No. 582,559, filed on May 30, 1975. Since there is an ever increasing demand for greater food production, animal growth-promoting agents are of considerable interest. Consequently, it is of prime importance to find processes suitable for large-scale manufacturing of said animal growth-promoting compounds in satisfactory yields.

In accordance with the process of the invention, it has been found that one of the alpha-methylene groups of a cycloalkanoheterocycle of formula (I) or benzocycloalkane of formula (II) set forth hereinbelow can be oxidized, albeit the presence of a nitrogen containing functional group, such as an amido or ureido group attached to the carbon atom of the second alpha-methylene group, so as to obtain in good yields the corresponding oxo compounds of formula (III) or (IV), respectively, as graphically illustrated:

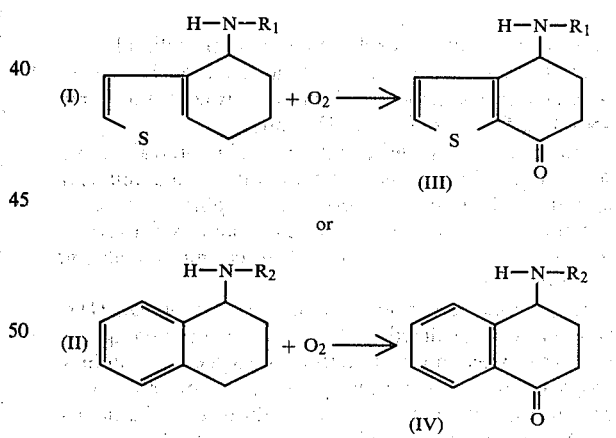

where $R_1$ and $R_2$ are each as defined above.

A preferred group of compounds represented by formula (I) or (II) above is that wherein $R_1$ and $R_2$ are each a radical selected from the group consisting of alkanoyl $C_1-C_7$, halogen-substituted alkanoyl $C_2-C_4$, benzoyl and

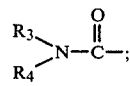

$R_3$ is a radical selected from the group consisting of hydrogen and alkyl $C_1-C_4$; $R_4$ is a radical selected from the group consisting of hydrogen and alkyl $C_1$-$C_8$, acetyl, trichloroacetyl and benzoyl; and where the

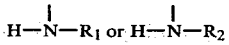

moiety is cyclized, each represents phthalimido; the racemic mixtures and the optical isomers thereof are oxidized in accordance with the process of the invention to the corresponding formula (III) of (IV), above.

Another preferred group of compounds represented by formula (I) or (II) above is that wherein $R_1$ and $R_2$ are each a radical selected from the group consisting of formyl, acetyl,

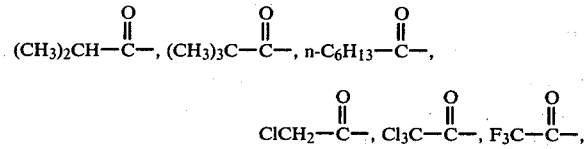

benzoyl and

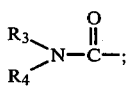

$R_3$ is a radical selected from the group consisting of hydrogen, methyl and iso-propyl; $R_4$ is a radical selected from hydrogen, methyl, n-octyl and benzoyl; and when the

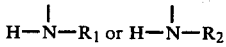

moiety is cyclized, each represents phthalimido; the racemic mixtures and the optical isomers thereof are oxidized by the process of the invention to the corresponding formula (III) or (IV), above.

As hereinabove indicated, the 4,5,6,7-tetrahydro-7-oxobenzo[b]thien-4-ylurea compounds of formula (III) and the 1,2,3,4-tetrahydro-4-oxo-1-naphthylurea compounds of formula (IV) are valuable and useful growth promoting agents for poultry, fur-bearing animals and farm animals.

In general, a compound represented by formula (I) or (II) above is oxidized with an oxygen-containing gas, such as oxygen, air or a mixture of oxygen and an inert gas, such as helium at atmospheric or superatmospheric pressure in the presence of a cobaltous or cobaltic salt catalyst in an organic solvent such as (a) a lower alkanoic acid or the anhydride thereof (b) a mixture of a lower alkanoic acid and an aliphatic or cycloaliphatic ketone, or (c) an aliphatic aldehyde other than formaldehyde, at a temperature range of 20° C. to 150° C. and, preferably, at from 25° C. to 120° C. The aforementioned reaction can be graphically illustrated as follows:

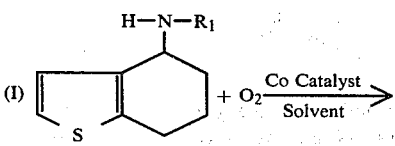

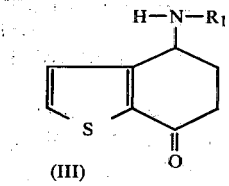

wherein $R_1$ and $R_2$ are each as defined above.

In the process above described, a compound of formula (I) or formula (II) is oxidized in a straightforward manner with oxygen, or with oxygen admixed with an inert gas such as nitrogen, helium, argon, neon, xenon and krypton, or with air and, preferably, with oxygen, oxygen-nitrogen mixtures and air, at pressures ranging from atmospheric to superatmospheric pressures usually up to 200 psig and, preferably, from 25 to 100 psig in the presence of a cobalt salt catalyst, such as $CoBr_2$ and $Co(OAc)_2$. However, the preferred catalyst is cobaltous acetate bromide (CAB), prepared by mixing approximately equimolar amounts of cobaltous acetate (or its tetrahydrate) and cobaltous bromide (or its tetrahydrate) with an appropriate amount of water in a $C_2$-$C_6$ alkanoic acid. Alternatively, it can be prepared from cobaltous acetate tetrahydrate and a solution of hydrogen bromide in acetic acid and in a $C_2$-$C_6$ alkanoic acid, or from cobaltous acetate tetrahydrate and aqueous hydrogen bromide in a mixture of a $C_2$-$C_6$ alkanoic acid and a $C_2$-$C_6$ alkanoic acid anhydride. The molar ratio of substrate to catalyst ranges from about 1:1 to 15:1 and, preferably, from about 1.5:1 to 6:1.

In general, the above reaction is carried out in an organic solvent selected from the group consisting of (a) a $C_2$-$C_6$ alkanoic acid, such as propionic or isobutyric acid, or the corresponding anhydride thereof, (b) a mixture of $C_2$-$C_6$ alkanoic acid, preferably acetic acid or isobutyric acid with an aliphatic ketone, such as acetone, methyl ethyl ketone, diethyl ketone, methyl isobutyl ketone, methyl isoamyl ketone and a cycloaliphatic ketone, such as cyclohexanone, or an aliphatic aldehyde other than formaldehyde, and (c) a mixture of a $C_2$-$C_6$ alkanoic acid, preferably, acetic acid or isobutyric acid, with t-butyl alcohol or acetonitrile at a temperature in the range of 20° C. to 150° C. and, preferably, from 25° C. to 120° C., at atmospheric pressure. When the reaction is carried out at a superatmospheric pressure, ambient temperature usually is sufficient, but the rate of the reaction can be increased by heating said reaction mixture. It has also been found that when the oxidation reaction of said novel process is carried out at near ambient temperature, then the rate of the reaction can be increased by introducing into the reaction mixture catalytic amounts of free radical initiators, such as azobisisobutyronitrile, hydrogen peroxide, t-butyl peroxide, dibenzoyl peroxide or peracids, such as peracetic acid and perbenzoic acid.

In the process hereinabove described, the uptake of oxygen can be conveniently followed by an oxygen analyzer, as well as by measuring the flow rates of oxygen entering and leaving the reaction mixture. The reaction is substantially complete when the oxygen uptake is no longer measureable. In addition, standard analytical procedures, such as gas chromatographic or high pressure liquid chromatographic analysis, can be used to check the completeness of the oxidation.

Thus, when $R_2$ is

and $R_3$ and $R_4$ are as hereinabove defined, the oxo compounds obtained by the above process are usually the desired animal growth promoting ureas, namely, 4,5,6,7-tetrahydro-7-oxobenzo[b]thien-4-ylureas of formula (VII) and 1,2,3,4-tetrahydro-4-oxo-1-naphthylureas of formula (VIII) as graphically illustrated below:

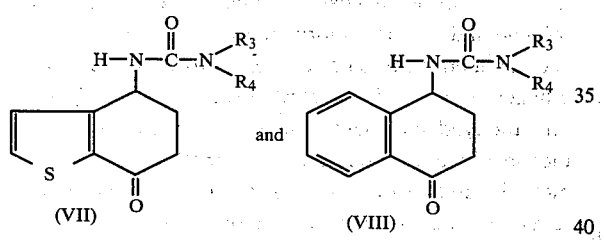

wherein $R_3$ is selected from the group consisting of hydrogen, and alkyl $C_1$-$C_4$; $R_4$ is hydrogen, alkyl $C_1$-$C_4$, alkanoyl $C_2$-$C_4$, halogen-substituted alkanoyl $C_2$-$C_4$ and

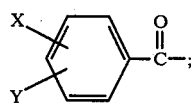

X and Y are selected from the group consisting of hydrogen, halogen, nitro and alkoxy $C_1$-$C_4$; the word "halogen" is used above to represent bromine, chlorine, fluorine and iodine; and said compounds are the racemic mixtures and the optical isomers thereof.

When $R_4$ is defined as alkanoyl $C_2$-$C_4$, halogen-substituted alkanoyl $C_2$-$C_4$ or

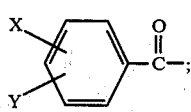

X and Y are as defined above, alkaline hydrolysis of these ureas affords ureas of formulae (VII) and (VIII) wherein $R_4$ is hydrogen.

However, when $R_2$ is not

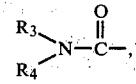

then the oxo compounds obtained by the above process are the corresponding formulae (III) and (IV) amides and imides, where

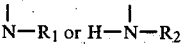

is each cyclized to form a moiety selected from the group of cyclic imides consisting of succinimido, maleimido and phthalimido. These amides and imides can be converted in a straightforward manner to the desired formula (VII) or (VIII) urea compound as follows: As amide (or imide) of formula (III) or formula (IV) is hydrolyzed with dilute acid or alkali, preferably an acid, e.g. hydrochloric acid to the corresponding formula (V) or formula (VI) amine (or a salt thereof) as hereinbelow graphically illustrated:

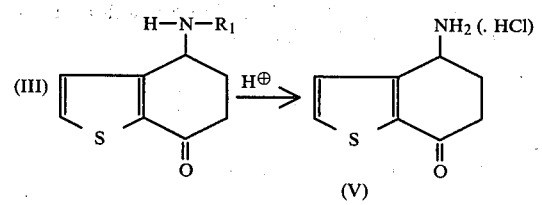

or

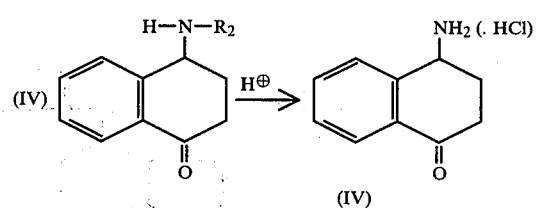

wherein $R_1$ and $R_2$ are each a radical selected from the group consisting of alkanoyl $C_1$-$C_6$, halogen-substituted alkanoyl $C_1$-$C_6$, carboalkoxy $C_1$-$C_4$,

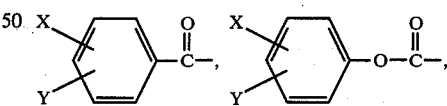

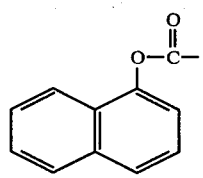

and

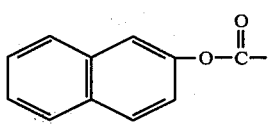

and when H-N-R$_1$ or H-N-R$_2$ is each cyclized, each represents a moiety selected from the group consisting of succinimido, maleimido and phthalimido; X and Y are selected from the group consisting of hydrogen, halogen, nitro and alkoxy C$_1$–C$_4$; said "halogen" denoting bromide, chlorine, fluorine and iodine and said compounds are the racemic mixtures and the optical isomers thereof.

Formula (VII) above, namely, 4,5,6,7-tetrahydro-7-oxobenzo[b]thien-4-ylurea compounds and formula (VIII) above, namely, 1,2,3,4-tetrahydro-4-oxo-1-naphthylurea compounds, wherein R$_3$ and R$_4$ are hydrogen can be advantageously prepared from the above-identified formula (V) or (VI) amines or acid salts thereof, by reacting said amines with an approximately equimolar amounts of sodium or potassium cyanate. However, it is generally preferable to employ from about 5% to about 50% excess of a suitable cyanate. The reaction can be conducted at atmospheric or superatmospheric pressure at a temperature in the range of 0° C. to 100° C., but is preferably conducted at atmospheric pressure at 0° C. to 70° C. in the presence of a solvent, such as water, C$_1$–C$_3$ aliphatic alcohol, tetrahydrofuran, dioxane, ethylene glycol dimethyl ether, acetone, methyl ethyl ketone, and mixtures thereof in the pH range of from 5 to 7 and, preferably, at pH 6. The above reaction may be graphically illustrated as follows:

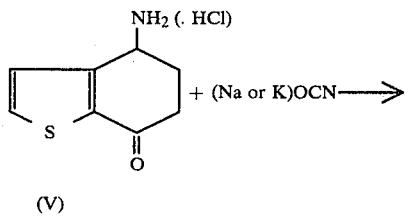

(V)

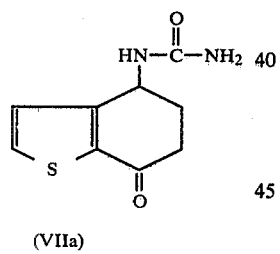

(VIIa)

or

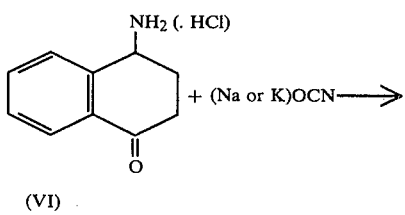

(VI)

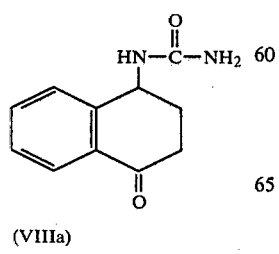

(VIIIa)

Substituted ureas of formula (VII) or (VIII) can be prepared advantageously by treating the above-identified amines of formulae (V) or (VI) with an appropriately substituted alkyl isocyanate of formula: R$_3$-NCO or with a carbamoyl halide of the formula

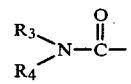

halide, wherein R$_3$ and R$_4$ are alkyl as hereinabove defined and the halide is chloro or bromo. The free bases of formula (V) or (VI) or the acid addition salts thereof, preferably the hydrochloride, can be employed in the presence of an acid acceptor. Illustrative acid acceptors are pyridine, triethylamine or any suitable tertiary amine, alkali metal carbonates, such as potassium carbonate and sodium carbonate, strong basic ion-exchange resins, and aqueous alkali. The reaction may be run from about 0° C. to 100° C. and, preferably, at 0° C. to 70° C. until the desired reaction is complete. The isocyanate or carbamoyl halide is generally employed in equimolar amounts, but it may be used in excess.

Exemplary organic solvents for the above reactions include: aprotic aromatic solvents, such as benzene, toluene and xylene; chlorinated hydrocarbon solvents, such as methylene chloride, chloroform and dichloroethane; ethers such as tetrahydrofuran, diethyl ether, dimethoxyethane, diethylene glycol dimethyl ether and dioxane; ketones such as acetone, methyl ethyl ketone, methyl butyl ketone, methyl isobutyl ketone; or mixtures of said solvents. The above reactions may be graphically illustrated as follows:

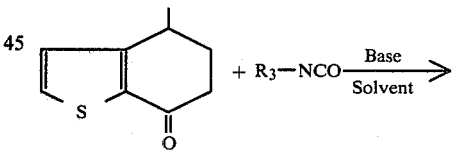

(V)

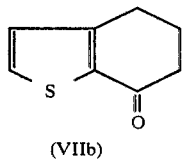

(VIIb)

or

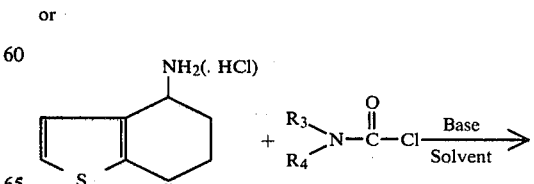

(V)

-continued

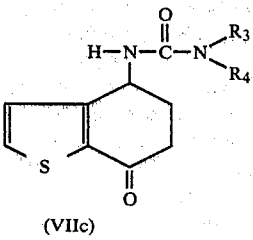
(VIIc)

and

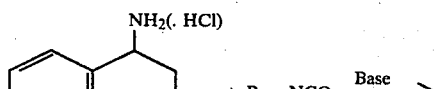
(VI)

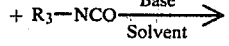
(VIIIb)

or

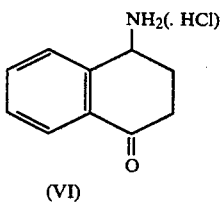 + 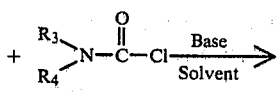
(VI)

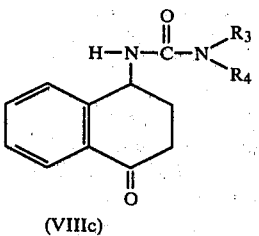
(VIIIc)

wherein R₃ and R₄ are as hereinabove defined.

All of the hereinbefore described preparations of 4,5,6,7-tetrahydro-7-oxobenzo[b]thiophene-, and 1,2,3,4-tetrahydro-4-oxonaphthalene derivatives yield racemic (dl) mixtures. The optically active isomers of the above compounds can be obtained by the resolution of the racemic (dl) formula (I) or (II) where R₂ is hydrogen, e.g. with (R)-(+)- and (S)-(−)-N-benzoylglutamic acids respectively, in sequence, and employing the thus obtained optically active isomers in subsequent reactions.

As stated above, formulae (VII) and (VIII) compounds are useful as growth promoting agents for animals, such as poultry, fur-bearing and farm animals, and the use of said compounds for this purpose provides the added advantage of improving feed conversion for said animals. The term "feed conversion" means the ratio of unit weight of feed per unit weight of gain and the improvement in feed conversion means increased weight gain from a given unit of feed consumed.

A growth-promoting amount of a formula (VII) or a formula (VIII) compound or an optically active isomer thereof is administered to a host animal in, or with, the animal's feed. Said compound may also be administered as a subcutaneous implant under the skin of said animal or as a parenteral injection. When administered in the feed of said animals, usually from about 0.0001% to about 0.08% by weight, and, preferably, from 0.001% to 0.04% by weight of formula (VII) or formula (VIII) urea, is effective for increasing growth rate and improving feed conversion. When administered as a parenteral injection or subcutaneous implant, usually in amounts that will supply about 0.0005 mg to about 0.2 mg, preferably 0.001 mg to 0.1 mg per kg of body weight per day of the active compound, it will produce the desired improvement in weight gain and will enhance feed conversion.

The practice of the present invention is further illustrated by the non-limiting examples set forth below.

EXAMPLE 1

Preparation of N-(4,5,6,7-tetrahydro-7-oxobenzo[b]thien-4-yl) acetamide

A mixture of N-(4,5,6,7-tetrahydrobenzo[b]thien-4-yl)-acetamide (2.0 g; 10.25 m mole), cobaltous acetate (0.49 g; 2.77 m mole), cobaltous bromide tetrahydrate (0.635 g; 2.18 m mole), water (0.4 ml), acetic acid (5.0 ml) and methyl isobutyl ketone (35.0 ml) in suitable flask fitted with a reflux condenser, a gas dispersion tube and a thermometer is stirred vigorously. Air is introduced through the dispersion tube into the turbid blue solution at room temperature for 45 minutes, and then the mixture is heated. After 25 minutes, the solution turns greenish blue (temperature: 45° C.) and in 15 minutes green (temperature: 55° C.). The reaction is run overnight with periodic additions of methyl isobutyl ketone. The greyish green reaction mixture containing some suspended dark gray solid is then diluted with water (40.0 ml) and saturated with sodium chloride. The upper organic phase is separated and the aqueous phase extracted with chloroform (2×100 ml). The organic phase and the chloroform extracts are combined, washed with brine (50 ml) and water (25 ml), respectively. The water wash is counter-extracted with chloroform (50 ml) and the chloroform extract added to the above organic phase. The combined organic phase is evaporated in vacuo to afford a gum, which contains the desired compound. The latter is hydrolyzed without further purification and the resultant amine hydrochloride is converted to 4,5,6,7-tetrahydro-7-oxobenzo[b]-thien-4-ylurea.

EXAMPLE 2

Preparation of 4,5,6,7-tetrahydro-7-oxobenzo[b]thien-4-ylurea

The crude material from Example 1 is stirred in a mixture of water (10.0 ml) and concentrated hydrochloric acid (10.0 ml) and heated at reflux for 4.3 hours. The reaction mixture is cooled, the solution decanted from the brown semisolid, which is then further washed with water (2×10 ml). The combined aqueous solutions are evaporated to afford brown crystals.

The above crystals are dissolved in water (10 ml), a solution of potassium cyanate (1.55 g; 19 m mole) in water (4 ml) added and the reaction mixture stirred overnight. The reaction mixture is then filtered, the solid collected is washed with water (70 ml) and methanol (10 ml) to attain 1.06 g of title compound, m.p. 234° C. to 236° C.

EXAMPLE 3

Preparation of N-(4,5,6,7-tetrahydro-7-oxobenzo[b]thien-4-yl)-acetamide

Oxygen is passed into a mixture of N-(4,5,6,7-tetrahydrobenzo[b]thien-4-yl)acetamide (1.0 g; 5.13 m mole), cobaltous acetate (0.25 g; 1.4 m mole), cobaltous bromide tetrahydrate (0.32 g; 1.1 m mole), isobutyric acid (20 ml) and water (0.2 ml) in a sintered glass funnel fitted with a condenser and thermometer, via the stem of the funnel. The dark brown mixture is oxygenated for 100 minutes at room temperature, then heated briefly to 48° C. After 2 hours and 10 minutes, the mixture is reheated to 50° C. and the flow of oxygen is terminated 2 hours later. The mixture is then worked up as described in Example 1 to attain a 37% yield of the title compound.

EXAMPLE 4

Preparation of 4,5,6,7-Tetrahydro-7-oxobenzo[b]thien-4-ylurea

A mixture of 4,5,6,7-tetrahydrobenzo[b]thien-4-ylurea (2.0 g), cobaltous acetate tetrahydrate (1.12 g), methyl isobutyl ketone (20 ml), acetic acid (20 ml) and a 30.2% solution of hydrobromic acid in acetic acid (0.9 ml) is shaken in a pressure bottle with 51 psig of oxygen. After 21.5 hours, the excess oxygen (33.2 psig) is vented and water (40 ml) added. The mixture is then saturated with sodium chloride and the organic phase is separated and washed well with brine. The organic phase is evaporated to dryness in vacuo to afford 2.62 g of oily solid. This material is stirred well with methanol (15 ml) and filtered to give 0.433 g of the title compound, m.p. 219° C. to 220° C.

EXAMPLE 5

Preparation of 4,5,6,7-tetrahydro-7-oxobenzo[b]thien-4-ylurea

A mixture of 4,5,6,7-tetrahydrobenzo[b]thien-4-ylurea (2.0 g), cobaltous acetate (0.49 g), cobaltous bromide tetrahydrate (0.635 g), water (0.4 ml), acetic acid (5 ml) and methyl isobutyl ketone (35 ml) is stirred and air is introduced via a capillary gas dispersion tube. The mixture is gradually heated to 45° C. and a deep green mixture is obtained. After heating overnight, the air flow is terminated and water (15 ml) added to the mixture. The mixture is saturated with sodium chloride and extracted with a 1:4 acetic acid: ethyl acetate mixture (3×50 ml). The combined extracts are washed once with water and evaporated to dryness in vacuo to afford 3.37 g of dark solid, which contains 15.8% of the title compound by high pressure liquid chromatographic analysis.

EXAMPLE 6

Preparation of N-(1,2,3,4-tetrahydro-4-oxo-1-naphthyl)formamide

A mixture of N-(1,2,3,4-tetrahydro-1-naphthyl)-formamide (2.0 g), cobaltous acetate tetrahydrate (0.95 g), a 30% solution of hydrobromic acid in acetic acid (0.925 g) and a 1:1 mixture of acetic acid: methyl isobutyl ketone (40 ml) is stirred and oxygen introduced via a capillary gas delivery tube. The blue reaction mixture is gradually heated to 76° C. in 42 minutes during which time the color changes to purple. The reaction mixture is then allowed to cool to room temperature. Water (40 ml) is added and the mixture saturated with sodium chloride. The mixture is extracted with chloroform (3×20 ml), the combined extracts are washed with saturated sodium chloride solution, dried over anhydrous magnesium sulfate and evaporated to dryness in vacuo. The residual red oil is triturated with ether and after cooling the title compound (0.4 g) collected. Further work-up of the mother liquor affords an additional 0.6 g of title compound.

EXAMPLE 7

Preparation of N-(1,2,3,4-tetrahydro-4-oxo-1-naphthyl)acetamide

A mixture of N-(1,2,3,4-tetrahydro-1-naphthyl)-acetamide (30 g), cobaltous acetate tetrahydrate (13.12 g), 30% hydrobromic acid in acetic acid (4.28 g), methyl isobutyl ketone (400 ml) and acetic acid (100 ml) is stirred and oxygen is introduced via a capillary gas dispersion tube. The mixture is heated gradually to 62° C. and the reaction is run 17 hours at 62° C. The reaction mixture is then cooled, the oxygen flow terminated and water (500 ml) is added. The mixture is extracted with chloroform (500 ml and 2×300 ml), the chloroform extracts are combined, washed with saturated sodium chloride solution and evaporated to dryness in vacuo. Benzene (200 ml) is added to the residue, the solution is filtered and the filtrate evaporated to dryness in vacuo to afford 40.3 g (damp) of the title compound.

EXAMPLE 8

Preparation of 1,2,3,4-Tetrahydro-4-oxo-1-naphthylurea

A mixture of crude N-(1,2,3,4-tetrahydro-4-oxo-1-naphthyl)acetamide (41.4 g), concentrated hydrochloric acid (300 ml) and water (250 ml) is heated at reflux overnight. The mixture is decanted, filtered and the cooled filtrate extracted with chloroform (300 ml). The aqueous solution is evaporated to dryness in vacuo and the residue dissolved in water (250 ml). A solution of potassium cyanate (21.8 g) in water (75 ml) is added dropwise to the aqueous solution and the reaction mixture stirred at room temperature for 72 hours. The title product is collected and dried to afford 21.45 g, m.p. 225° C. dec.

EXAMPLE 9

Preparation of 1,2,3,4-Tetrahydro-4-oxo-1-naphthylurea

A mixture of 1,2,3,4-tetrahydro-1-naphthylurea (1.9 g), cobaltous acetate tetrahydrate (1.08 g), 30% hydrobromic acid in acetic acid (0.9 ml) and a 1:1 mixture of methyl ethyl ketone: acetic acid (30 ml) is shaken in a pressure vessel under 31 psig of oxygen for 7.5 hours. The vessel is then vented, the contents are mixed with an equal volume of water and extracted with chloroform (2×25 ml). The combined chloroform extracts are dried over anhydrous magnesium sulfate and evaporated to dryness in vacuo to afford 2.34 g solid. The solid is washed with cold methanol (30 ml) to afford 0.75 g of title compound, m.p. 210° C. to 214° C.

EXAMPLES 10 TO 21

Preparation of N-(4,5,6,7-tetrahydro-7-oxobenzo[b]thien-4-yl) acetamide

By following the procedure of Example 1 in every detail except that reaction parameters are varied in the following reactions which are summarized in Table I, below.

TABLE I $$\underset{(I)}{\text{[structure with NH-CCH}_3\text{ on tetrahydrobenzothiophene]}} \xrightarrow[\Delta;\ \text{Solvent}]{O_2/CAB} \underset{\text{III}}{\text{[7-oxo product]}}$$

| Example | I m mole | CAB m mole | Maximum Temp. °C. | Solvent ml | III Yield |
|---|---|---|---|---|---|
| 10 | 10.25 | 4.4 | 65 | 10 $(CH_3CO)_2O$/30 $CH_3COOH$ | 50 |
| 11 | 10.25 | 4.4 | 48 | 10 $(CH_3CO)_2O$/30 $CH_3COOH$ | * |
| 12 | 25.6 | 4.4 | 50 | 10 $(CH_3CO)_2O$/30 $CH_3COOH$ | ** |
| 13 | 51.28 | 4.4 | 56 | 10 $(CH_3CO)_2O$/30 $CH_3COOH$ | 30 |
| 14 | 10.25 | 4.4 | 73 | 40 $CH_3CN$/2 $CH_3COOH$ | 33.5 |
| 15 | 10.25 | 4.4 | 70 | 40 $CH_3COOH$/5 $H_2O$ | 35 |
| 16 | 5.13 | 2.2 | 73 | 20 $CH_3COOH$ | 32 |
| 17 | 5.13 | 2.2 | 50 | 20 $(CH_3)_2CH-COOH$ | 37 |
| 18 | 10.25 | 4.4 | 58 | 40 $(CH_3)_3C-OH$/2 $CH_3COOH$ | 39 |
| 19 | 10.25 | 4.4 | 45 | 40 $CH_3-\overset{O}{\overset{\|}{C}}-C_2H_5$/2 $CH_3COOH$ | 42 |
| 20 | 10.25 | 4.4 | 45–56.5 | 35 $CH_3COCH_2CH(CH_3)_2$ | 60.5 |
| 21 | 76.9 | 16.4 | 50 | 97.5 $CH_3COCH_2CH(CH_3)_2$ | 58 |

*Not isolated, converted to the urea in 32% overall yield.
**Not isolated, converted to the urea in 29% overall yield.

EXAMPLES 22 TO 48

Preparation of Various Ketoamides from the Corresponding Amides

By the procedure of Example 4, the following amides are oxidized to the ketoamides as summarized in Table (II) below:

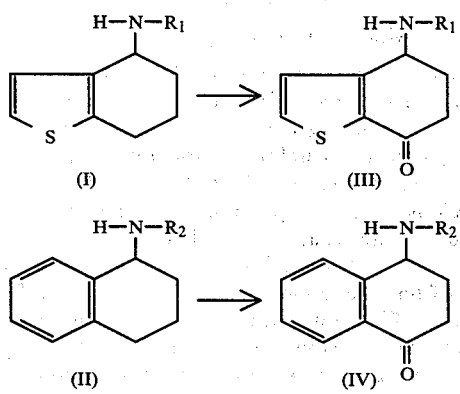

where $R_1$ and $R_2$ are each as hereinbelow defined. The starting materials (I) and (II) are prepared by allowing the corresponding amines of (I) and (II), respectively, to react with $R_2$ acid anhydrides or $R_2$ acid chlorides/$Et_3N$ in benzene.

TABLE II

| Examples | Starting Material | $R_1$ or $R_2$ | Product |
|---|---|---|---|
| 22 | I | $(CH_3)_3-\overset{O}{\overset{\|}{C}}-$ | III |
| 23 | I | $(CH_3)_2CH-\overset{O}{\overset{\|}{C}}-$ | III |
| 24 | I | benzoyl | III |
| 25 | I | p-chlorobenzoyl | III |
| 26 | I | o-chlorobenzoyl | III |
| 27 | I | m-chlorobenzoyl | III |
| 28 | I | $\underset{\text{[phthaloyl]}}{O=C\diagdown\ \diagup C=O}$ * | III |
| 29 | I | $O=C-CH_2-CH_2-C=O$ | III |
| 30 | I | $O=C-CH=CH-C=O$ | III |
| 31 | I | —CHO | III |
| 32 | I | $n-C_5H_{11}\overset{O}{\overset{\|}{C}}-$ | III |
| 33 | I | p-methoxybenzoyl | III |
| 34 | II | —CHO | IV |
| 35 | II | $(CH_3)_3C-\overset{O}{\overset{\|}{C}}-$ | IV |
| 36 | II | benzoyl | IV |
| 37 | II | 4-n-butoxybenzoyl | IV |
| 38 | II | 3,4-dichlorobenzoyl | IV |
| 39 | II | 2-Methoxybenzoyl | IV |
| 40 | II | 4-nitrobenzoyl | IV |
| 41 | I | 3,4-dichlorobenzoyl | III |
| 42 | I | 4-nitrobenzoyl | III |
| 43 | I | 3-n-butoxybenzoyl | III |
| 44 | I | $CH_3-O-\overset{O}{\overset{\|}{C}}-$ | III |
| 45 | I | $n-C_4H_9O-\overset{O}{\overset{\|}{C}}-$ | III |
| 46 | II | $Cl_3C-\overset{O}{\overset{\|}{C}}-$ | IV |
| 47 | II | $F_3C-\overset{O}{\overset{\|}{C}}-$ | IV |

TABLE II-continued

| Examples | Starting Material | $R_1$ or $R_2$ | Product |
|---|---|---|---|
| 48 | I | 2-chloro-4-nitrobenzoyl | III |

*Wherein $R_2$ is a bifunctional acid, thus H—N—$R_2$ represents the moiety:phthalimido.

EXAMPLE 49

Preparation of N-(4,5,6,7-tetrahydro-7-oxobenzo[b]thien-4-yl)acetamide

A mixture of N-(4,5,6,7-tetrahydrobenzo[b]thien-4-yl)-acetamide (2.0 g), cobaltous acetate tetrahydrate (1.12 g), azo-bis-isobutyronitrile (0.05 g), a 30% solution of hydrobromic acid in acetic acid (0.9 ml) and isobutyric acid (40 ml) is stirred and oxygen bubbled through via a gas dispersion tube. The dark blue mixture gradually turns green and the temperature rises from 25° C. to 28° C. After 6.3 hours, the flow of oxygen is terminated and water (40 ml) added to the reaction mixture. The mixture is then saturated with sodium chloride, the organic phase is separated, the aqueous phase is extracted with chloroform (3×80 ml) and the chloroform extracts combined with the organic phase. The combined organic phase is washed with saturated sodium chloride solution and then evaporated to dryness. The residue is dissolved in chloroform, the solution is washed with saturated sodium carbonate solution (10 ml) and then evaporated to dryness in vacuo to afford 2.46 g of solid, which on analysis by high pressure liquid chromatography (HPLC) is shown to contain the title compound amounting to a yield of 51.3%.

Similarly, use of air instead of pure oxygen in the above reaction affords the title compound in 49.6% yield as determined by HPLC.

EXAMPLE 50

Preparation of N-(1,2,3,4-tetrahydro-4-oxo-1-naphthyl)acetamide

A solution of N-(1,2,3,4-tetrahydro-1-naphthyl) acetamide (189.3 g) in methyl isobutyl ketone (2.54 l) and acetic acid (635 ml) is mixed with cobaltous acetate tetrahydrate (83 g) and a solution of 30% hydrobromic acid in acetic acid (65 ml). The blue reaction mixture is stirred and heated and oxygen bubbled through at the rate of 453.3 ml/min and nitrogen is passed over the reaction mixture as a blanket and to dilute the outflowing oxygen. The effluent gas contains 15.5% oxygen as measured by an oxygen analyzer. After 30 minutes, as the mixture is heated the oxygen consumption becomes noticeable at about 48° C. and the blue mixture begins to turn green. The flow rate of oxygen is then increased until the oxygen uptake stops in about 0.5 hours. The temperature is allowed to rise to 93° C. After oxygen is no longer consumed, the mixture is cooled, diluted with water (3 l), and the organic phase separated. The aqueous phase is extracted with chloroform (1000 ml and 2×500 ml) and the extracts combined with the organic phase. The combined organic solutions are washed with saturated sodium chloride solution (2 l) and dried over anhydrous magnesium sulfate. The organic solution is then evaporated to dryness in vacuo to afford 219 g of solid, which contains 68.2% of the title compound by HPLC assay.

EXAMPLE 51

The following compounds of formula "A" are prepared by acylating 4,5,6,7-tetrahydrobenzo[b]thiophen-4-amine with the respective acid chlorides or anhydrides in the presence of pyridine or triethylamine. Subsequently, the thus obtained compounds of formula "A" are oxidized by the procedure of Example 1 to afford compounds of formula "B" as summarized in Table III, below.

TABLE III

"A" (H—NR$_1$) $\xrightarrow{O_2/CAB}$ "B" (H—N—R$_1$, with ketone)

| $R_1$ | Melting Point °C. "A" | Melting Point °C. "B" |
|---|---|---|
| C$_6$H$_5$—C(=O)— | 124–125.5 | 181–184 |
| (CH$_3$)$_3$C—C(=O)— | 128–130 | 142–145 |
| (CH$_3$)$_2$CH—C(=O)— | 153–155 | 130–133 |
| Cl$_3$—C—C(=O)— | 90–94 | 174–177 |
| CF$_3$—C(=O)— | 127–128 | 161–164 |
| phthaloyl (O=C—C$_6$H$_4$—C=O)* | 166–167.5 | 166–168 |
| CH$_3$O—C(=O)— | 100–102 | 140–142 |

*wherein $R_1$ is a bifunctional acid, thus H—N—$R_1$ forms the phthalimido moiety.

EXAMPLE 52

Mouse Growth Regulant Tests

CFI female mice from Carworth Farm are received when they are six weeks old. They are housed ten to a cage in air-conditioned rooms (72°–76° F.) with automatically controlled lights, 14 hours on and 10 hours off. The basal diet used in these studies is Purina Laboratory Chow (see description below), which is supplied ad libitum. Water is also allowed ad libitum.

Thirteen days after arrival, the mice are weighed in groups of ten and assigned at random to the different treatments. The concentration of the different compounds in the diet is indicated in the following Tables. Twelve days later the mice are weighed again and the experiment terminated. At least three cages (30 mice) of untreated controls are included in each test. Test data are provided in Table IV below, wherein data are reported as percent weight gain over controls. The following is a description of the diet to which the growth-promoting compounds are added.

| DIET | |
|---|---|
| GUARANTEED ANALYSIS | |
| Crude protein not less than | 23.0% |
| Crude fat not less than | 4.5% |
| Crude fiber not more than | 6.0% |
| Ash not more than | 9.0% |
| INGREDIENTS | |
| Meat and bone meal, dried skimmed milk, wheat germ meal, fish meal, animal liver meal, dried beet pulp, ground extruded corn, ground oat groats, soybean meal, dehydrated alfalfa meal, cane molasses, animal fat preserved with BHA, vitamin $B_{12}$ supplement, calcium pantothenate, choline chloride, folic acid, riboflavin supplement, brewers' dried yeast, thiamin, niacin, vitamin A supplement, D activated plant sterol, vitamin E supplement, calcium carbonate, dicalcium phosphate, iodized salt, ferric ammonium citrate, iron oxide, manganous oxide, cobalt carbonate, copper oxide, zinc oxide. | |

TABLE IV

Effectiveness of
1,2,3,4-Tetrahydro-4-oxo-1-naphthylureas as
Animal Growth-Promoting Agents Reported as Percent
Weight Gain Over Controls Using
Mice as the Test Animal

| Rate ppm in Diet | $R_3$ | $R_4$ | % Weight Gain Over Controls |
|---|---|---|---|
| 50 | H | H | 35.71 |
| 100 | H | H | 97.40 |
| 200 | H | H | 93.51 |
| 200 | $CH_3$ | H | 69.00 |
| 400 | $2-C_4H_9$ | H | 19.00 |

Similarly in the same growth promotion test, at 200 ppm in the diet, 4,5,6,7-tetrahydrobenzo[b]thien-4-ylurea, 4,5,6,7-tetrahydro-7-oxobenzo[b]thien-4-ylurea, and 1,2,3,4-tetrahydro-1-naphthylurea, respectively, give 132.2%, 117% and 66.8% weight gain over controls.

EXAMPLE 53

The following compounds of formula "A" are prepared by acylating 1,2,3,4,-tetrahydro-1-naphthylamine with the respective acid chlorides or anhydrides in the presence of pyridine or triethylamine. Subsequently, the compounds are oxidized by the procedure of Example 1 to afford compounds of formula "B" as summarized in Table V.

TABLE V

| | Melting Point °C. | |
|---|---|---|
| $R_2$ | "A" | "B" |
| $n-C_6H_{13}CO$ | 69–73 | Not Purified* |
| $C_6H_5CO$ | 113–117 | Not Purified* |
| | 123–129 | 143–157 |

*Converted to VIII where $R_3$, $R_4$ = hydrogen.
**Wherein $R_2$ is a bifunctional acid anhydride, thus $H-\overset{|}{N}-R_2$
represents the phthalimido moiety.

EXAMPLE 54

Preparation of
N-(4,5,6,7-tetrahydro-7-oxobenzo[b]thien-4-yl)
acetamide

A mixture of N-(4,5,6,7-tetrahydrobenzo[b]thien-4-yl acetamide (2.0 g), cobaltous acetate tetrahydrate (1.12 g), methyl isobutyl ketone (20 ml), acetic acid (20 ml) and a 30.2% solution of hydrobromic acid in acetic acid (0.95 ml) is shaken in a pressure bottle with 79.2 psig of oxygen. After 16 hours, the excess oxygen (70.1 psig) is vented and water (40 ml) added. The mixture is extracted with chloroform (3×40 ml) and the combined extracts are washed with brine and evaporated to dryness in vacuo to afford 2.98 g of an oil. HPLC analysis shows the title compound is present amounting to a 57.3% yield.

Similarly, use of cobaltous acetate recovered from the above chloroform extracted aqueous solution via evaporation gives a 51.5% yield of the title compound by HPLC analysis.

By the above procedure N-(1,2,3,4-tetrahydro-1-naphthyl)acetamide affords a 64.5% yield of N-(1,2,3,4-tetrahydro-4-oxo-1-naphthyl)acetamide.

EXAMPLE 55

Preparation of
Substituted-4,5,6,7-tetrahydro-7-oxobenzo[b]-thien-4-ylureas

By the method described in Example 4, following compounds are prepared.

| $R_3$ | $R_4$ | m.p. °C. |
|---|---|---|
| $CH_3$ | $CH_3$ | 195–197 |
| H | $C_8H_{17}$ | 105–108 |

-continued

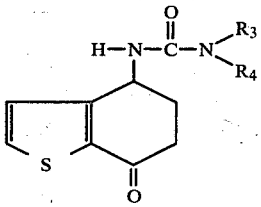

| R₃ | R₄ | m.p. °C. |
|---|---|---|
| H | CH₃ | 212–215 |
| (CH₃)₂CH | H | 180–187 |

EXAMPLE 56
Preparation of
(−)-N-(4,5,6,7-tetrahydro-7-oxobenzo[b]thien-4-yl)acetamide In the manner described in Example 7, (−)-N-(4,5,6,7-tetrahydrobenzo[b]thien-4-yl)acetamide is oxidized to give the title compound.

Similarly, (−)-4,5,6,7-tetrahydrobenzo[b]thien-4-yl-urea is oxidized to afford (−)-4,5,6,7-tetrahydro-7-oxobenzo[b]-thien-4-yl urea, m.p. 247°–249.5° C. (dec.).

EXAMPLE 57
Preparation of
(−)-1,2,3,4-tetrahydro-4-oxo-1-naphthylurea

In the manner described in Example 9, (−)-1,2,3,4-tetrahydro-1-naphthylurea is oxidized to afford the title compound, mp.p 237°–240° C.

Similarly, (−)-N-(1,2,3,4-tetrahydro-1-naphthyl)-acetamide is oxidized to afford (−)-N-(1,2,3,4-tetrahydro-4-oxo-1-naphthyl)acetamide, melting point 147° C. to 157° C.

EXAMPLE 58
Preparation of
1-Benzoyl-3-(4,5,6,7-tetrahydro-7-oxobenzo[b]-thien-4-yl)urea In the manner described in Example 4, 1-benzoyl-3-(4,5,6,7-tetrahydrobenzo[b]thien-4-yl)urea, m.p. 187° C. to 190° C., is oxidized to afford the title compound, m.p. 204°–207° C.

Similarly, the following compounds are prepared:

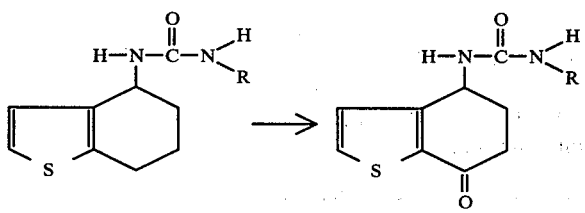

where R is defined as: CH₃CO,Cl₃C—CO, F₃C—CO, 4—Cl—C₆H₄CO, 4—O₂N—C₆H₄CO, 2—CH₃O—C₆H₄CO, 2—CH₃O—C₆H₄CO, 4—CH₃O—C₆H₄CO, 2—ClC₆H₄CO, 3—Cl—C₆H₄CO—, 2—O₂N—C₆H₄CO, 3—O₂N—C₆H₄CO, or 2—C₃H₇CO.

The starting materials are prepared by allowing 4,5,6,7-tetrahydrobenzo[b]thiophen-4-amine to react with the requisite isocyanate or by allowing 4,5,6,7-tetrahydrobenzo[b]thien-4-yl isocyanate to react with the requisite amide.

Alkaline hydrolysis of these ketoureas affords 4,5,6,7-tetrahydro-7-oxobenzo[b]thien-4-ylurea.

EXAMPLE 59
By following the procedure of Example 4 the following carbamates are oxidized to the ketocarbamates:

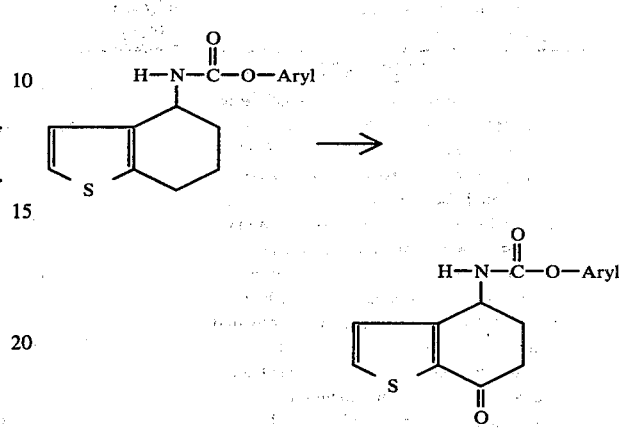

where aryl is phenyl, 2- or 3- or 4-isomers of chlorophenyl, nitrophenyl, tolyl, methoxyphenyl, 2,4-dichlorophenyl, alpha- or beta-naphthyl or 2,4-dinitrophenyl.

The starting materials are readily prepared by the addition of the requisite phenols to 4,5,6,7-tetrahydrobenzo-[b]thien-4-yl isocyanate.

EXAMPLE 60
Preparation of
4,5,6,7-Tetrahydro-7-oxobenzo[b]thien-4-ylurea and 1,2,3,4,-tetrahydro-4-oxo-1-naphthylurea A 3 g sample of 1-benzoyl-3-(4,5,6,7-tetrahydro-7-oxobenzo[b]thien-4-yl)urea is stirred in 10 ml of 1 N NaOH and the mixture is heated at reflux for 6 hr. An additional 5 ml of 1 N NaOH is then added and the mixture is heated for another hour. The mixture is cooled to room temperature and the title compound is collected by filtration and washed well with H₂O. The title compound is dried to afford 1.71 g, m.p. 241° C. to 244° C.

Substitution of 1-benzoyl-3-(4,5,6,7-tetrahydro-7-oxobenzo[b]thien-4-yl)urea with 1-acetyl- or 1-trichloroacetyl-3-(4,5,6,7-tetrahydro-7-oxobenzo[b]thien-4-yl)urea in the above hydrolysis also affords the title compound.

In the same manner, 1-benzoyl-3-(1,2,3,4-tetrahydro-4-oxo-1-naphthyl)urea is hydrolyzed to afford 1,2,3,4-tetrahydro 4-oxo-1-naphthylurea, m.p. 241° C. to 244° C.

EXAMPLE 61
Preparation of
1-Benzoyl-3-(4,5,6,7-tetrahydrobenzo[b]thien-4-yl)urea and 1-benzoyl-3-(1,2,3,4-tetrahydro-1-naphthyl)urea A 2.94 g sample of benzoyl isocyanate in 5 ml of CH₂Cl₂ is added to 3.04 g of 4,5,6,7-tetrahydrobenzo[b]thiophen-4-amine in 50 ml of CH₂Cl₂ under N₂ atmosphere. After stirring overnight at room temperature, the reaction mixture is evaporated to dryness in vacuo. The residue is then stirred in 100 ml of Et₂O and filtered to afford 1-benzoyl-3-(4,5,6,7-tetrahydrobenzo[b]thien-4-yl)urea, m.p. 189° C. to 194° C. Substitution of trichloroacetyl isocyanate for benzoyl isocyanate affords 1-trichloroacetyl-3-(4,5,6,7-tetrahydrobenzo[b]thien-4-yl)urea. Use of 4,5,6,7-tetrahydrobenzo[b]thien-4-ylisocyanate and acetamide in the above manner affords 1-acetyl-3-(4,5,6,7-tetrahydrobenzo[b]thien-4-yl)urea.

In the same manner, substitution of 1,2,3,4-tetrahydro-1-naphthylamine for 4,5,6,7-tetrahydrobenzo[b]thiophen-4-amine affords 1-benzoyl-, and 1-trichloroacetyl-3-(1,2,3,4-tetrahydro-1-naphthyl)urea when benzoyl isocyanate and trichloroacetyl isocyanate are used. Use of 1,2,3,4-tetrahydro-1-naphthylisocyanate and acetamide in the same manner affords 1-acetyl-3-(1,2,3,4-tetrahydro-1-naphthyl)urea.

EXAMPLE 62

Preparation of 4,5,6,7-Tetrahydrobenzo[b]thien-4-ylurea and 1,2,3,4-tetrahydro-1-naphthylurea In the manner described in Example 60, 1-benzoyl-3-(4,5,6,7-tetrahydrobenzo[b]thien-4-yl)urea and 1-benzoyl-3-(1,2,3,4-tetrahydro-1-naphthyl)urea are hydrolyzed to afford 4,5,6,7-tetrahydrobenzo[b]thien-4-ylurea, m.p. 204.5° C. to 208.5° C., and 1,2,3,4-tetrahydro-1-naphthylurea, m.p. 212° C. to 214° C.

EXAMPLE 63

Preparation of N-(1,2,3,4-Tetrahydro-4-oxo-1-naphthyl)acetamide

In 40 ml of HOAc and 6 ml of acetaldehyde, 3.78 g of N-(1,2,3,4-tetrahydro-1-naphthyl)acetamide; 2.24 g of $Co(OAc)_2.4 H_2O$, and 1.76 ml of 30% HBr in HOAc are shaken in a glass pressure vessel on a Paar apparatus under 38 psig of $O_2$. The mixture is heated to 86° C. over a 0.5 hr. period and gradually allowed to cool. The mixture is then shaken at room temperature for 18.5 hr and 50 ml of $H_2O$ is added after the $O_2$ is vented. The mixture is extracted with $CHCl_3$ (3×50 ml) and the combined organic phases are dried over $MgSO_4$ and evaporated to dryness in vacuo. The residue is then triturated with 100 ml of $Et_2O$, stirred for 18 hours and the crude title compound is collected by filtration. This gives 2.12 g of the title compound, m.p. 104° C. to 115° C.

Substitution of acetaldehyde in the above reaction with propionaldehyde, butyraldehyde, isobutyraldehyde or octyladehyde also affords the title compound. Similarly, substitution of N-(4,5,6,7-tetrahydrobenzo[b]thien-4-yl)acetamide for N-(1,2,3,4-tetrahydro-1-naphthyl)acetamide in the above-mentioned procedure affords N-(4,5,6,7-tetrahydro-7-oxobenzo[b]thien-4-yl)acetamide.

We claim:

1. A process for the preparation of a compound of the formula:

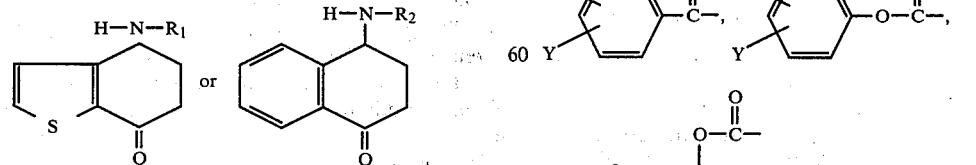

wherein $R_1$ and $R_2$ are each a substituent selected from the group consisting of alkanoyl $C_1$-$C_7$, halogen-substituted alkanoyl $C_1$-$C_7$, carboalkoxy $C_1$-$C_4$,

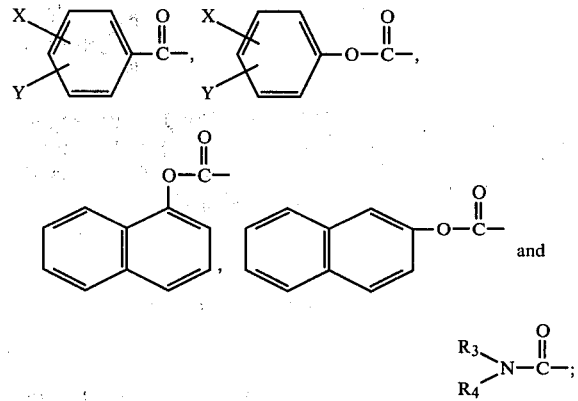

$R_3$ is a radical selected from the group consisting of hydrogen and alkyl $C_1$-$C_4$, $R_4$ is a substituent selected from the group consisting of hydrogen, alkyl $C_1$-$C_8$, alkanoyl $(C_2$-$C_4)$, halogen-substituted alkanoyl $(C_2$-$C_4)$, halogen-substituted alkanoyl $(C_2$-$C_4)$ and

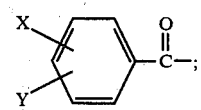

and when the

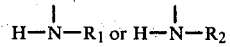

moiety is cyclized, each represents a moiety selected from the group consisting of succinimido, maleimido and phthalimido, X and Y are each a radical selected from the group consisting of hydrogen, fluorine, chlorine, bromine iodine, nitro, alkyl $C_1$-$C_4$; the racemic mixtures and the optical isomers thereof; comprising the steps of: subjecting a compound of the formula:

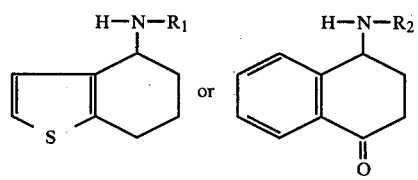

wherein $R_1$ and $R_2$ are each a radical selected from the group consisting of alkanoyl $C_1$-$C_7$, halogen-substituted alkanoyl $C_1$-$C_7$, carboalkoxy $C_1$-$C_7$, -continued

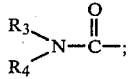

$R_3$ is selected from the group consisting of hydrogen and alkyl ($C_1$–$C_4$); $R_4$ is selected from the group consisting of hydrogen, alkyl ($C_1$–$C_8$), alkanoyl ($C_2$–$C_4$), and halogen-substituted alkanoyl ($C_2$–$C_4$), and

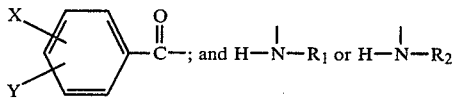

is each cyclized, each represents a moiety selected from the group consisting of succinimido, maleimido and phthalimido; X and Y are selected from the group consisting of hydrogen, halogen, nitro, alkyl $C_1$–$C_4$ and alkoxy ($C_1$–$C_4$); the racemic mixtures and the optical isomers thereof; to the action of an oxygen containing gas at positive pressures up to about 100 psig and at a temperature ranging from about 20° C. to about 150° C. in the presence of a cobalt catalyst selected from the group consisting of a cobaltous salt and a cobaltic salt, said catalyst being present in a solvent-substrate mixture, wherein said catalyst is present in said mixture in a molar ratio of 1:1 to 15:1, and said solvent being selected from the group consisting of a ($C_2$–$C_6$) alkanoic acid, a mixture of a ($C_2$–$C_6$) alkanoic acid and a ($C_2$–$C_6$) alkanoic acid anhydride, a mixture of a ($C_2$–$C_6$) alkanoic acid and an aliphatic ketone, a mixture of a ($C_2$–$C_6$) alkanoic acid and a cycloaliphatic ketone, a mixture of a ($C_2$–$C_6$) alkanoic acid and an aliphatic aldehyde other than formaldehyde, a mixture of a ($C_2$–$C_6$) alkanoic acid and t-butyl alcohol and a mixture of a ($C_2$–$C_6$) alkanoic acid and acetonitrile, for a period of time sufficient to essentially complete the reaction, and thereafter recovering said resultant oxidized product.

2. The process according to claim 1, wherein $R_1$ and $R_2$ are each selected from the group consisting of alkanoyl $C_1$–$C_6$, halogen-substituted alkanoyl $C_2$–$C_3$, carboalkoxy $C_1$–$C_4$,

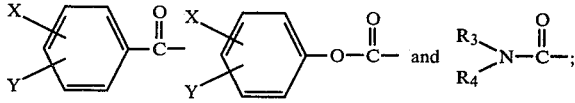

$R_3$ is selected from the group consisting of hydrogen and alkyl $C_1$–$C_2$; $R_4$ is selected from the group consisting of hydrogen, alkyl $C_1$–$C_4$, alkanoyl ($C_2$–$C_4$), halogen-substituted alkanoyl ($C_2$–$C_4$) and

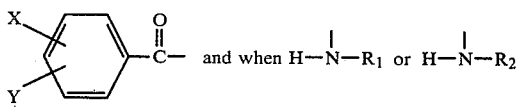

is cyclized, each represents a moiety selected from the group consisting of succinimido, maleimido and phthalimido; X and Y are selected from hydrogen, chlorine, nitro, methyl and methoxy; the racemic mixtures and the optical isomers thereof; the oxidizing agent is oxygen, oxygen-nitrogen mixtures or air; the pressure ranges from atmospheric pressure 100 psig; the catalyst is cobaltous acetate bromide, said catalyst being present in a solvent substrate:catalyst molar ratio of 1.5:1 to 6:1; the alkanoic acid is a $C_2$–$C_4$ alkanoic acid; the anhydride is a $C_2$–$C_4$ alkanoic acid anhydride; the aliphatic ketone is methyl ethyl ketone and methyl iso-butyl ketone.

3. The process according to claim 1, wherein $R_1$ and $R_2$ are each selected from the group consisting of alkanoyl $C_1$–$C_7$, halogen-substituted alkanoyl $C_2$–$C_4$; benzoyl and

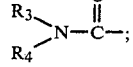

$R_3$ is selected from hydrogen and alkyl $C_1$–$C_4$ $R_4$ is selected from hydrogen, alkyl $C_1$–$C_8$, alkanoyl ($C_2$–$C_4$), and benzoyl; and when

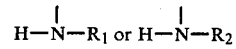

is cyclized, each are taken together with nitrogen represents phthalimido; the racemic mixtures and the optical isomers thereof; the oxidizing agent is oxygen, oxygen-nitrogen mixtures or air; the pressure ranges from atmospheric pressure to 100 psig; the catalyst is cobaltous acetate bromide, said catalyst being present in a solvent substrate:catalyst molar ratio of 1.5:1 to 6:1; the alkanoic acid is a $C_2$–$C_4$ alkanoic acid; the anhydride is a $C_2$–$C_4$ alkanoic acid anhydride; the aliphatic ketone is methyl ethyl ketone and methyl iso-butyl ketone.

4. The process according to claim 1, wherein $R_1$ and $R_2$ each is selected from the group consisting of formyl, acetyl,

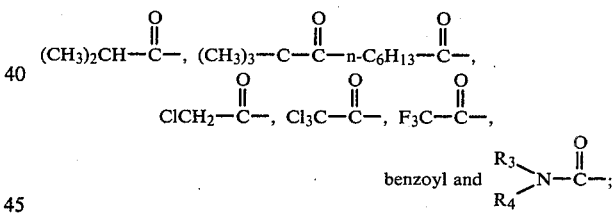

$R_3$ is selected from the group consisting of hydrogen, methyl and iso-propyl; and $R_4$ is selected from the group consisting of hydrogen, methyl, n-octyl, acetyl, trichloroacetyl and benzoyl.

5. The process according to claim 1, wherein the solvent is selected from the group consisting of acetic acid, propionic acid, butyric acid and isobutyric acid.

6. The process according to claim 1, wherein the solvent is a mixture of acetic acid and tertiary butyl alcohol.

7. The process according to claim 1, wherein the solvent is a mixture of acetic acid and acetonitrile.

8. The process according to claim 1, wherein the solvent is a mixture of acetic acid and diethyl ketone.

9. The process according to claim 1, wherein the solvent is a mixture of acetic acid and methyl isobutyl ketone.

10. The process according to claim 1, wherein the solvent is a mixture of acetic acid and methyl isoamyl ketone.

11. The process according to claim 1 wherein a compound of the formula:

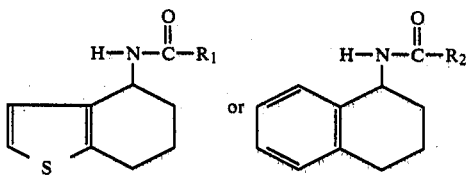

wherein $R_1$ and $R_2$ are each selected from the group consisting of hydrogen, methyl, ethyl, propyl, isopropyl, t-butyl and phenyl; is subjected to oxidation in the presence of a cobalt catalyst to obtain a compound of the formula:

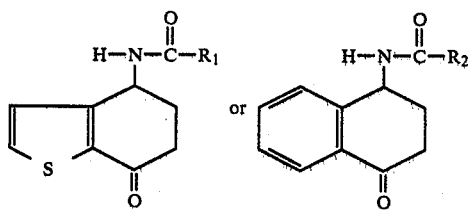

12. The process according to claim 1, wherein the compound to be oxidized is N-(4,5,6,7-tetrahydrobenzo[b]thien-4-yl)-acetamide.

13. The process according to claim 1, wherein the compound to be oxidized is (−)-N-(4,5,6,7-tetrahydrobenzo[b]thien-4-yl)acetamide.

14. The process according to claim 1, wherein the compound to be oxidized is 4,5,6,7-tetrahydrobenzo[b]thien-4-ylurea.

15. The process according to claim 1, wherein the compound to be oxidized is (−)-4,5,6,7-tetrahydrobenzo[b]thien-4-ylurea.

16. The process according to claim 1, wherein the compound to be oxidized is N-(1,2,3,4-tetrahydro-1-naphthyl)-acetamide.

17. The process according to claim 1, wherein the compound to be oxidized is (−)-N-(1,2,3,4-tetrahydro-1-naphthyl) acetamide.

18. The process according to claim 1, wherein the compound to be oxidized is 1,2,3,4-tetrahydro-1-naphthylurea.

19. The process according to claim 1, wherein the compound to be oxidized is (−)-1,2,3,4-tetrahydro-1-naphthylurea.

20. The process according to claim 1, wherein the compound to be oxidized is N-(4,5,6,7-tetrahydrobenzo[b]thien-4-yl)-phthalimide.

21. The process according to claim 1, wherein the compound to be oxidized is N-(1,2,3,4-tetrahydro-1-naphthyl)-phthalimide.

22. The process according to claim 1, wherein the compound to be oxidized is N-(4,5,6,7-tetrahydrobenzo[b]thien-4-yl-formamide.

23. The process according to claim 1, wherein the compound to be oxidized is N-(1,2,3,4-tetrahydro-1-naphthyl)-formamide.

24. The process according to claim 1, wherein the compound to be oxidized is 1-benzoyl-3-(4,5,6,7-tetrahydrobenzo[b]thien-4-yl)urea.

25. The process according to claim 1, wherein the compound to be oxidized is 1-benzoyl-3-(1,2,3,4-tetrahydro-1-naphthyl)urea.

* * * * *